United States Patent
Oz et al.

(10) Patent No.: US 10,213,120 B2
(45) Date of Patent: *Feb. 26, 2019

(54) SYSTEMS, APPARATUSES AND METHODS FOR SENSING FETAL ACTIVITY

(71) Applicant: Nuvo Group Ltd., Ramat Gan (IL)

(72) Inventors: Oren Oz, Modiin (IL); Amit Kam, Tel Aviv (IL); Nathan Intrator, Tel Aviv (IL)

(73) Assignee: Nuvo Group Ltd., Ramat Gan (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/439,487

(22) Filed: Feb. 22, 2017

(65) Prior Publication Data
US 2017/0156607 A1 Jun. 8, 2017

Related U.S. Application Data (63) Continuation of application No. 15/071,915, filed on Mar. 16, 2016, now Pat. No. 9,642,544, which is a (Continued)

(51) Int. Cl.
*A61B 5/024* (2006.01)
*A61B 5/00* (2006.01)
(Continued)

(52) U.S. Cl.
CPC ........ *A61B 5/02411* (2013.01); *A61B 5/0245* (2013.01); *A61B 5/0255* (2013.01); *A61B 5/02405* (2013.01); *A61B 5/04014* (2013.01); *A61B 5/04017* (2013.01); *A61B 5/0444* (2013.01); *A61B 5/0456* (2013.01); *A61B 5/04525* (2013.01); *A61B 5/4362* (2013.01); *A61B 5/6823* (2013.01); *A61B 5/7203* (2013.01); *A61B 5/725* (2013.01);
(Continued)

(58) Field of Classification Search
CPC ..... A61B 5/02411; A61B 7/04; A61B 5/7221; A61B 5/7203; A61B 5/7253; A61B 5/7278

See application file for complete search history.

(56) References Cited

U.S. PATENT DOCUMENTS 3,187,098 A 6/1965 Farrar et al.
4,781,200 A * 11/1988 Baker ................ A61B 5/02411
600/483

(Continued)

FOREIGN PATENT DOCUMENTS

CN 2358833 Y 1/2000
CN 102137622 A 7/2011
(Continued)

OTHER PUBLICATIONS

Supplementary European Search Report to corresponding EP Application No. 16764297 dated Sep. 13, 2018 (8 pages).
(Continued)

*Primary Examiner* — Catherine Voorhees
(74) *Attorney, Agent, or Firm* — Greenberg Traurig, LLP (57) ABSTRACT

The invention provides systems and methods for monitoring the wellbeing of a fetus by the non-invasive detection and analysis of fetal cardiac activity data, utilizing a plurality of acoustic sensors.

10 Claims, 9 Drawing Sheets

Related U.S. Application Data continuation-in-part of application No. 14/921,489, filed on Oct. 23, 2015, now Pat. No. 9,392,952.

(60) Provisional application No. 62/133,485, filed on Mar. 16, 2015.

(51) Int. Cl.
| | | |
|---|---|---|
| *A61B 5/04* | (2006.01) | |
| *A61B 7/04* | (2006.01) | |
| *A61B 5/0255* | (2006.01) | |
| *A61B 5/0245* | (2006.01) | |
| *A61B 5/0444* | (2006.01) | |
| *A61B 5/0452* | (2006.01) | |
| *A61B 5/0456* | (2006.01) | |

(52) U.S. Cl.
CPC ............ *A61B 5/726* (2013.01); *A61B 5/7221* (2013.01); *A61B 5/7253* (2013.01); *A61B 5/7278* (2013.01); *A61B 7/04* (2013.01)

(56) References Cited

U.S. PATENT DOCUMENTS

| | | | |
|---|---|---|---|
| 5,467,775 A | 11/1995 | Callahan et al. | |
| 6,171,263 B1 | 1/2001 | Sullivan | |
| 6,749,573 B2 | 6/2004 | Bryant et al. | |
| 6,954,971 B1 | 10/2005 | Bryant et al. | |
| 7,333,850 B2 * | 2/2008 | Marossero | A61B 5/02411 600/511 |
| 9,642,544 B2 * | 5/2017 | Oz | A61B 5/02411 |
| 9,713,430 B2 * | 7/2017 | Oz | A61B 5/0444 |
| 2001/0034490 A1 | 10/2001 | Bryant et al. | |
| 2005/0267376 A1 | 12/2005 | Marossero et al. | |
| 2007/0118054 A1 * | 5/2007 | Pinhas | A61B 5/1102 600/587 |
| 2007/0260155 A1 | 11/2007 | Rapoport et al. | |
| 2017/0172426 A1 * | 6/2017 | Oz | A61B 5/0245 |

FOREIGN PATENT DOCUMENTS

| | | |
|---|---|---|
| CN | 102772222 A | 11/2012 |
| CN | 203988040 U | 12/2014 |
| CN | 104306018 A | 1/2015 |
| EP | 0454931 A1 | 11/1991 |
| WO | 0160245 A2 | 8/2001 |
| WO | 2014192002 A1 | 12/2014 |

OTHER PUBLICATIONS

Najafabadi et al., "Fetal heart rate monitoring based on independent component analysis," Computers in Biology and Medicine, vol. 36, No. 3, pp. 241-252 (2006).

Vaisman et al., "Passive fetal monitoring by adaptive wavelet denoising method," Computers in Biology and Medicine, vol. 42, No. 2, pp. 171-179 (2012).

Varady, P., "Wavelet-based adaptive denoising of phonocardiographic records," 2001 Conference Proceedings of the 23rd Annual International Conference of the IEEE Engineering in Medicine and Biology Society, vol. 3, pp. 1846-1849 (2001).

European Supplemental Search Report to corresponding EP Application No. 16764295 dated Nov. 26, 2018 (8 pages).

\* cited by examiner

SYSTEMS, APPARATUSES AND METHODS FOR SENSING FETAL ACTIVITY

This application is a continuation of U.S. patent application Ser. No. 15/071,915 filed, Mar. 16, 2016, which is a continuation-in-part of U.S. patent application Ser. No. 14/921,489, filed on Oct. 23, 2015, now U.S. Pat. No. 9,392,952, which claims priority to U.S. Provisional Patent Application No. 62/133,485, filed on Mar. 16, 2015, the entire contents of all of which are incorporated by reference herein in their entirety.

FIELD OF THE INVENTION

The invention relates generally to systems and methods for monitoring the wellbeing of a fetus by the non-invasive detection and analysis of fetal cardiac activity data.

BACKGROUND

Monitoring fetal cardiac activity can be useful to determine the health of a fetus during pregnancy.

SUMMARY

In some embodiments, the instant invention is directed to a computer-implemented method which includes at least the steps of: receiving, by at least one computer processor executing specific programmable instructions configured for the method, a plurality of Phonocardiogram (PCG) signals data inputs from a plurality of acoustic sensors; digital signal filtering, by the at least one computer processor, utilizing a plurality of bandpass filters, the plurality of PCG signals data inputs to form a plurality of filtered PCG outputs, where the plurality of bandpass filters includes a L number of bandpass filters, where each bandpass filter outputs a K number of filtered PCG outputs; wavelet denoising, by the at least one computer processor, a first subset of filtered PCG outputs of the plurality of filtered PCG outputs to form a M number of denoised filtered PCG outputs, where M is equal to L multiply by K; transforming, by the at least one computer processor, utilizing an Independent-Component-Analysis (ICA), a second subset of filtered PCG outputs of the plurality of filtered PCG outputs to form the M number of filtered ICA transforms; transforming, by the at least one computer processor, utilizing the Independent-Component-Analysis (ICA), a first portion of the second subset of denoised filtered PCG outputs to form the M number of filtered denoised filtered ICA transforms; compiling, by the at least one computer processor, a S number of a plurality of detection heartbeat (DH) inputs, including: i) the M number of filtered PCG outputs, ii) the M number of denoised filtered PCG outputs, iii) the M number of filtered ICA transforms, and iv) the M number of denoised filtered ICA transforms; detecting, by the at least one computer processor, beat locations of beats in each of DH inputs; calculating, by the at least one computer processor, a confidence score that describes a probability that the beats in each DH input of the plurality of DH inputs represent actual heartbeats and not a noise; dividing, by the at least one computer processor, the plurality of DH inputs into at least two groups: i) a first group of DH inputs containing fetal heartbeats, ii) a second group of DH inputs containing maternal heartbeats selecting, by the at least one computer processor, from the first group of DH inputs, at least one particular fetal DH input that contains the fetal heartbeat based on a first confidence score of the at least one particular fetal DH input; and selecting, by the at least one computer processor, from the second group of DH inputs, at least one particular maternal DH input that contains the maternal heartbeat, based on a second confidence score of the at least one particular maternal DH input.

In some embodiments, where the wavelet denoising includes at least: deconstructing, by the at least one computer processor, each filtered PCG output to generate a plurality of transform coefficients, by irrelatively passing each filtered PCG output through a succession of low and high pass filters; identifying, by the at least one computer processor, a subset of heartbeat-carrying transform coefficients from the plurality of transform coefficients, reconstructing, by the at least one computer processor, the subset of heartbeat-carrying transform coefficients to form the M number of denoised filtered PCG outputs.

In some embodiments, K is equal to a number of the plurality of acoustic sensors, and L is equal to 6.

In some embodiments, each filter of the plurality of bandpass filters has a bandwidth of 10-100 Hz and a frequency range of 5-110 HZ.

In some embodiments, the detecting of the beat locations of the beats in each of DH inputs includes at least: calculating, by the at least one computer processor, a predetermined transform filter; iteratively repeating, by the at least one computer processor, based on a predetermined average window length of the predetermined transform filter: identifying, in each DH input, a subset of peaks having a predetermined shape and a predetermined size, and selecting a group of peaks from the subset of peaks, where the group of peaks has the smallest variance measure; calculating, by the at least one computer processor, initial locations of the beats.

In some embodiments, the calculating the confidence score includes at least: generating, by the at least one computer processor, a beat-by-beat heartbeat graph for each DH input based on the beat locations.

In some embodiments, the dividing the plurality of DH inputs into the first group of DH inputs containing fetal heartbeats and the second group of DH inputs containing maternal heartbeats includes at least: clustering, by the at least one computer processor, the beats of each DH input according to each beat value; and assigning, by the at least one computer processor, a particular DH input having a higher average beat rate into the first group of DH inputs containing fetal heartbeats.

In some embodiments, the present invention is directed to a specifically programmed computer system, including at least the following components: at least one specialized computer machine, including: a non-transient memory, electronically storing particular computer executable program code; and at least one computer processor which, when executing the particular program code, becomes a specifically programmed computing processor that is configured to at least perform the following operations: receiving a plurality of Phonocardiogram (PCG) signals data inputs from a plurality of acoustic sensors; digital signal filtering, utilizing a plurality of bandpass filters, the plurality of PCG signals data inputs to form a plurality of filtered PCG outputs, where the plurality of bandpass filters includes a L number of bandpass filters, where each bandpass filter outputs a K number of filtered PCG outputs; wavelet denoising a first subset of filtered PCG outputs of the plurality of filtered PCG outputs to form a M number of denoised filtered PCG outputs, where M is equal to L multiply by K; transforming, utilizing an Independent-Component-Analysis (ICA), a second subset of filtered PCG outputs of the plurality of filtered PCG outputs to form the M number of filtered ICA transforms; transforming, utilizing the Independent-Component-Analysis (ICA), a first portion of the second subset of denoised filtered PCG outputs to form the M number of denoised filtered ICA transforms; compiling a S number of a plurality of detection heartbeat (DH) inputs, including: i) the M number of filtered PCG outputs, ii) the M number of denoised filtered PCG outputs, iii) the M number of filtered ICA transforms, and iv) the M number of denoised filtered ICA transforms; detecting beat locations of beats in each of DH inputs; calculating a confidence score that describes a probability that the beats in each DH input of the plurality of DH inputs represent actual heartbeats and not a noise; dividing the plurality of DH inputs into at least two groups: i) a first group of DH inputs containing fetal heartbeats, ii) a second group of DH inputs containing maternal heartbeats; selecting, from the first group of DH inputs, at least one particular fetal DH input that contains the fetal heartbeat based on a first confidence score of the at least one particular fetal DH input; and selecting, from the second group of DH inputs, at least one particular maternal DH input that contains the maternal heartbeat, based on a second confidence score of the at least one particular maternal DH input.

DETAILED DESCRIPTION

For clarity of disclosure, and not by way of limitation, the detailed description of the invention is divided into the following subsections that describe or illustrate certain features, embodiments or applications of the present invention.

In some embodiments, the present invention provides a system for detecting, recording and analyzing acoustic data from a pregnant mother carrying a fetus to discern cardiac data of mother and/or fetus. In some embodiments, a plurality of acoustic sensors is used to record phonocardiogram (PCG) signals, representative of cardiac activity data. The phonocardiogram signals are recordings of all the sounds made by the heart during a cardiac cycle due to, typically, for example, vibrations created by closure of the heart valves. For instance, there can be at list two sound generating events: the first when the atrioventricular valves close at the beginning of systole (S1) and the second when the aortic valve and pulmonary valve close at the end of systole (S2).

In some embodiments, the exemplary inventive system of the present invention can utilize a plurality of acoustic sensors (e.g., 2, 3, 4, 5, 6, 7, 8, 9, 10, etc.) to be positioned on and/or near the abdomen of a pregnant woman. For example, in some embodiments, the acoustic sensors are directly attached. In some embodiments, the acoustic sensors are incorporated into an article, such as, for example, a belt, a patch, and the like, and the article is worn by, or placed on, the pregnant mother. In some embodiments, the recorded acoustic signal data from the plurality of acoustic sensors is transmitted via, for example, at least one communication link, originated by at least one data transmitter resided in the article, to at least one remote server for the processing by at least one specifically programmed computer processor in accordance with the principles of the present invention. In some embodiments, the communication link is based on at least one wireless-type communication implementations (e.g., low emission Bluetooth (Bluetooth Low Energy). In some embodiments, the exemplary system of the present invention for recording, detecting and analyzing acoustic signal data includes an analog pre-processing module, an analog to digital converter/microcontroller (ADC/MCU) module, a communications module, a smartphone module, and a cloud computing module. In some embodiments, the analog pre-processing module performs at least one function selected from the group consisting of: amplification of the recorded signals, and filtering the recorded signals. In some embodiments, the ADC/MCU module performs at least one task selected from the group consisting of: converting analog signals to digital signals, converting the recorded signals to digital signals, compressing the data, digital filtering, and transferring the recorded PCG signals data to the transmitter. In some embodiments, the communications module transmits the recorded signals to a wireless receiver of the system of the present invention.

In some embodiments, the choice of acoustic sensors is readily determined by one of ordinary skill in the art. Factors influencing acoustic sensor choice include, but are not limited to, the sensitivity of the microphone component, the size of the acoustic sensor, the weight of the acoustic sensor, and the like. In some embodiments, the acoustic sensor is configured to compensate for the changes in sound propagation caused by the skin-air interface. Acoustic signals comprise sound waves or vibrations that propagate as a mechanical wave of pressure and displacement, through a medium such as air, water, or the body. Without intending to be limited to any particular theory, the behavior of sound propagation can be affected by the relationship between the density and pressure of the medium though which the sound wave propagates. Also, the behavior of sound propagation can be affected by the motion of the medium though which the sound wave propagates. Furthermore, the behavior of sound propagation can be affected by the viscosity of the medium though which the sound wave propagates.

Figure 1:
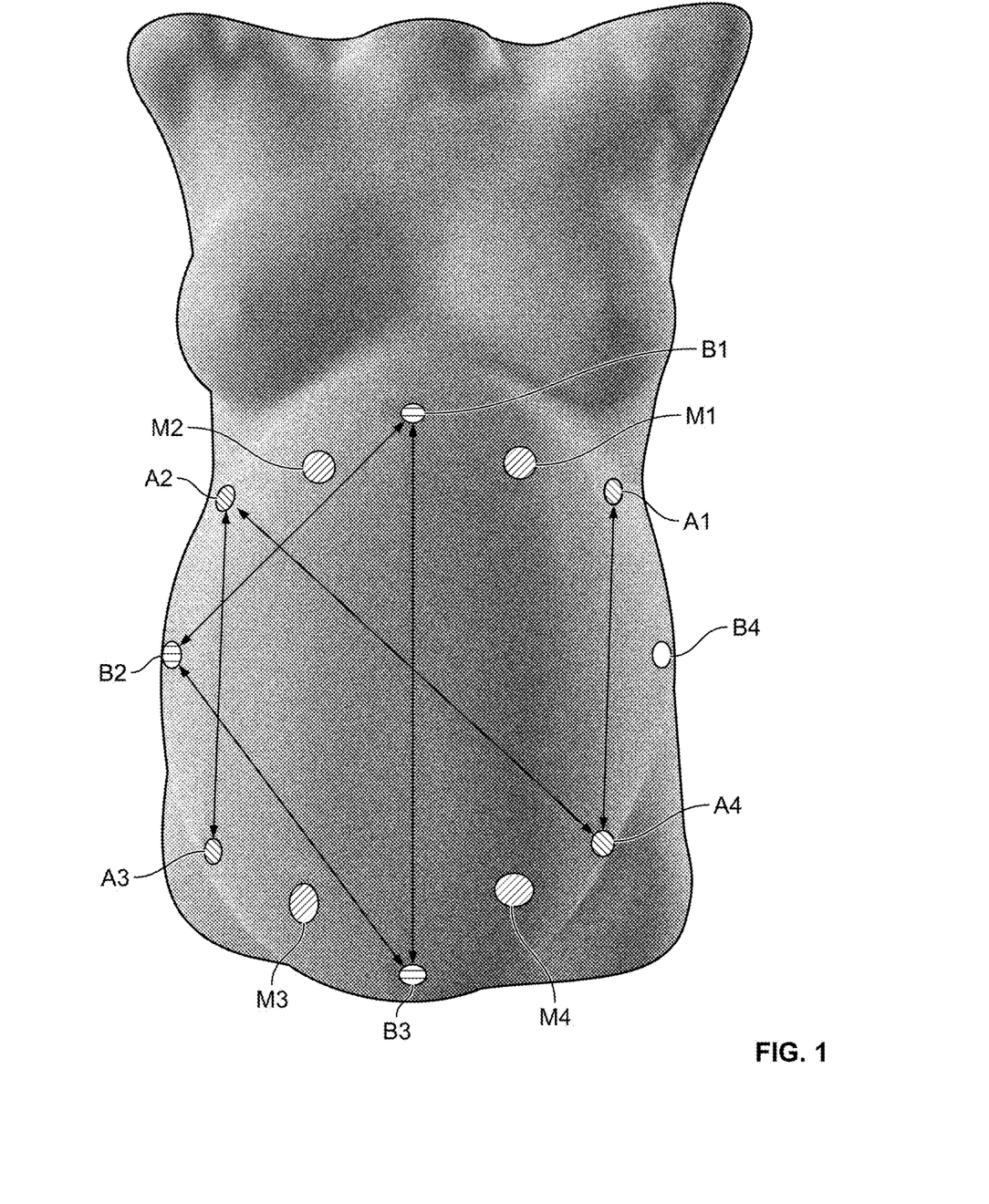
FIG. 1 shows the positions of the exemplary acoustic sensors on the abdomen of a pregnant woman according to some embodiments of the present invention.

For example, as shown in FIG. 1, the exemplary inventive system of the present invention utilizes a set of four acoustic sensors (M1-M4) at respective exemplary positions. In some embodiments, the positioning of acoustic sensors can varies based, at least in part, on, for example, shape of mother's stomach, the stage of the pregnancy, physiological characteristics of mother and/or fetus(es), previous acoustic and/or other types of cardio recordings (e.g., Electrocardiogram (ECG) signal recordings and analysis, etc.), and other similarly suitable data.

In some embodiments, the acoustic sensors of the present invention record the internal sound produced inside the woman with added noise from the environment. As detailed below, from these recordings the heartbeat sound of the fetus(es) and/or the mother are extracted and the heart rate of each subject is calculated.

In some embodiments, the level of detection by each acoustic sensor is independent of the other acoustic sensors (e.g, in FIG. 1, on other three acoustic sensors). Referring to FIG. 1, in some embodiments, it is determined that, typically, the fetus PCG signals are detected by the acoustic sensors in locations M3 and/or M4, while the maternal PCG signals are detected by the acoustic sensors in locations M1 and/or M2. In some embodiments, the maternal PCG signals can be detected by all four sensors (M1-M4) and have to be cleaned in order to detect the fetus(es) heartbeats. In some embodiments, as detailed below, the cleaning process is performed using at least one Independent component analysis (ICA) algorithm of the present invention. For instance, in some embodiments, the inventive system of the present invention assumes that the interfering noises are audio sources which are not the fetal origin that thus are statistically independent from the fetal heart sounds.

Figure 2:
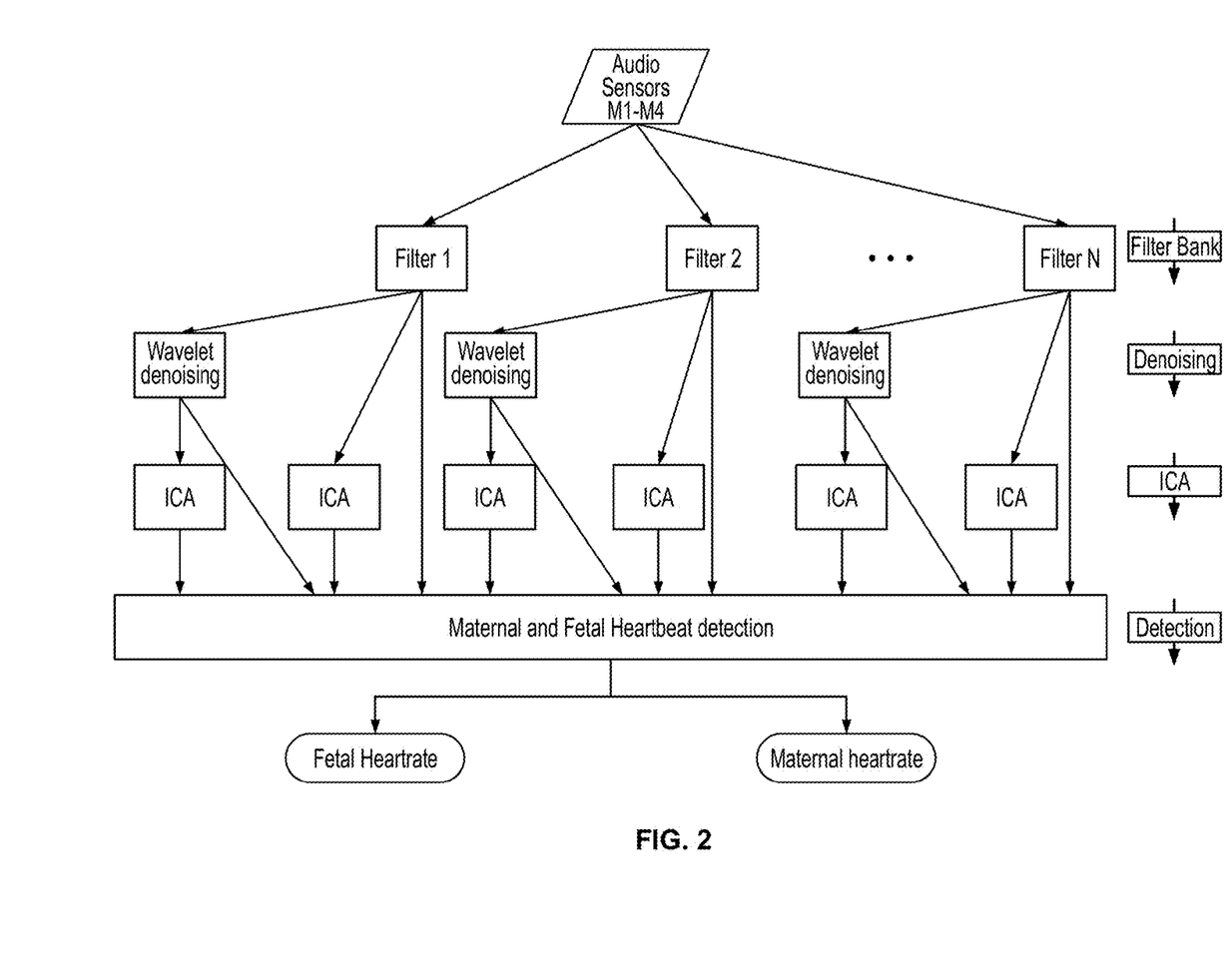
FIG. 2 shows a flow chart of an algorithm used to detect and analyze cardiac activity data according to some embodiments of the present invention.

An Example of an Illustrative Process Utilized to Estimate the Fetus(es) and/or Maternal Heartbeat Data in Accordance with the Present Invention FIG. 2 shows an exemplary process utilized, in some embodiments, by the exemplary inventive system of the present invention to estimate the fetus(es) and/or maternal heartbeat data (e.g., presence of heartbeats, heartbeat patterns, heartbeat frequency, etc.).

Referring to FIG. 2, the illustrative process contains at the following four stages.

Stage 1: Filter Bank

Referring to FIG. 2, the input is the signal data recorded by each acoustic sensor (M1-M4) shown in FIG. 1. In some embodiments, the recorded signal data from each of the four acoustic sensors is passed through, for example but not limited to, L number of bandpass filters, where each filter has a predetermine frequency range. In some embodiments, the exemplary six bandpass filters (L=6) can have the following six bandwidths:

10-45 Hz
20-50 Hz
25-65 Hz
40-80 Hz
55-95 Hz
20-80 Hz.

In some embodiments, there can be at least 3 bandpass filters. In some embodiments, there can be between 3-12 bandpass filters. In some embodiments, there can be between 5-10 bandpass filters. In some embodiments, there can be at least 5 bandpass filter. In some embodiments, there can be at least 7 bandpass filter.

In some embodiments, the bandwidth of a particular filter can be selected from a range of 10-100 Hz. In some embodiments, the bandwidth of a particular filter can be selected from a range of 20-100 Hz. In some embodiments, the bandwidth of a particular filter can be selected from a range of 30-100 Hz. In some embodiments, the bandwidth of a particular filter can be selected from a range of 40-100 Hz. In some embodiments, the bandwidth of a particular filter can be selected from a range of 50-100 Hz. In some embodiments, the bandwidth of a particular filter can be selected from a range of 60-100 Hz. In some embodiments, the bandwidth of a particular filter can be selected from a range of 70-100 Hz. In some embodiments, the bandwidth of a particular filter can be selected from a range of 80-100 Hz. In some embodiments, the bandwidth of a particular filter can be selected from a range of 90-100 Hz.

In some embodiments, a particular filter can have a frequency range of 5-110 Hz. In some embodiments, a particular filter can have a frequency range of 15-110 Hz. In some embodiments, a particular filter can have a frequency range of 25-110 Hz. In some embodiments, a particular filter can have a frequency range of 35-110 Hz. In some embodiments, a particular filter can have a frequency range of 45-110 Hz. In some embodiments, a particular filter can have a frequency range of 55-110 Hz. In some embodiments, a particular filter can have a frequency range of 5-105 Hz. In some embodiments, a particular filter can have a frequency range of 5-100 Hz. In some embodiments, a particular filter can have a frequency range of 5-95 Hz. In some embodiments, a particular filter can have a frequency range of 5-25 Hz. In some embodiments, a particular filter can have a frequency range of 5-50 Hz. In some embodiments, a particular filter can have a frequency range of 5-75 Hz.

In some embodiments, referring to FIG. 2, a K number of outputs (filtered PCG outputs) from each of the six filters are forwarded to the second stage. For example, in some embodiments, detailed below, K is equal to, but not limited to, 4. In some embodiments, K is equal to the number of acoustic sensors (M1-M4) being used to collect the acoustic sensor data. In some embodiments, a predetermined number of outputs is forwarded to the second stage.

Stage 2: Wavelet Denoising

In some embodiments, for example, one of the four filtered PCG outputs from the six bandpass filters is further subject to wavelet denoising, where such particular filtered PCG output is deconstructed by passing through a succession of low and high pass filters up to X times to form the deconstructed filtered PCG output. In some embodiments, the value of X depends on a sampling frequency which allows to achieve suitable results to meet requirements detailed below. For example, in some embodiments, the particular filtered PCG output is deconstructed by passing through a succession of low and high pass filters up to 3 times. For example, in some embodiments, the particular filtered PCG output is deconstructed by passing through a succession of low and high pass filters up to 5 times. For example, in some embodiments, the particular filtered PCG output is deconstructed by passing through a succession of low frequency pass and high frequency pass filters up to 6 times.

Figure 3A:
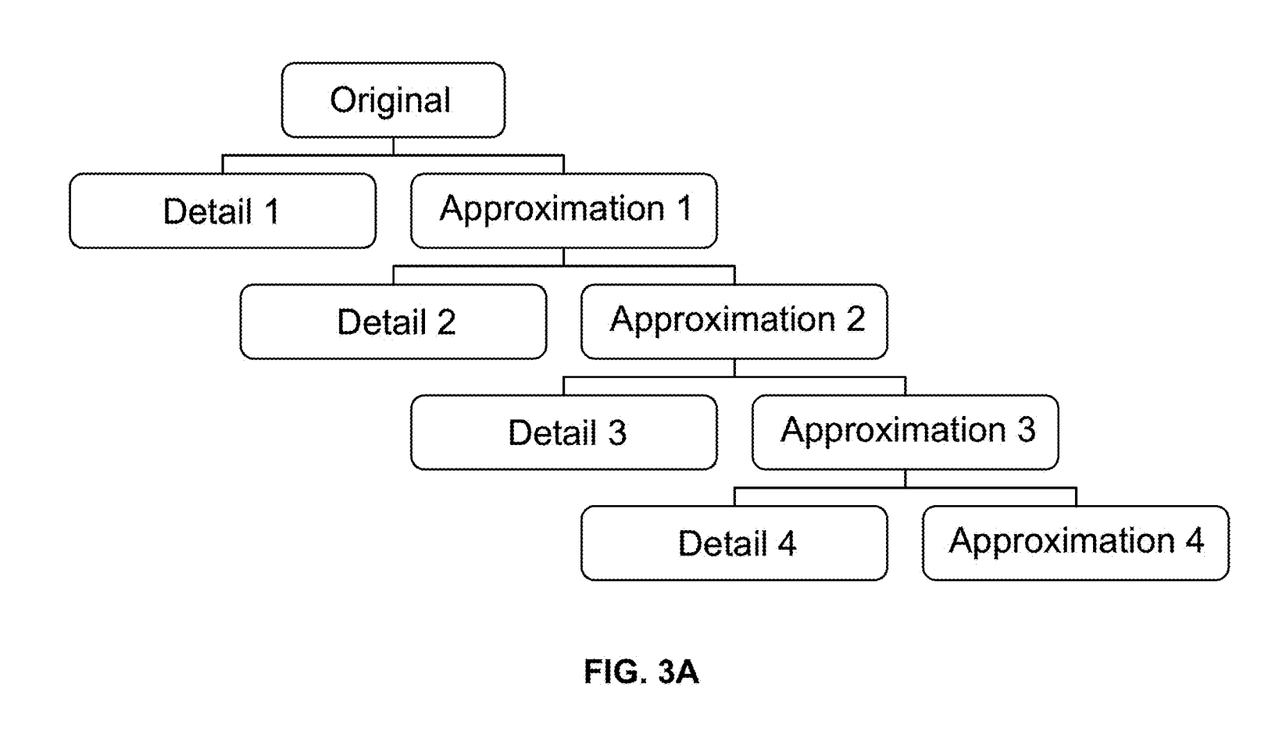
FIGS. 3A and 3B show flow charts of a signal denoising algorithm according to some embodiments of the present invention.
Figure 3B:
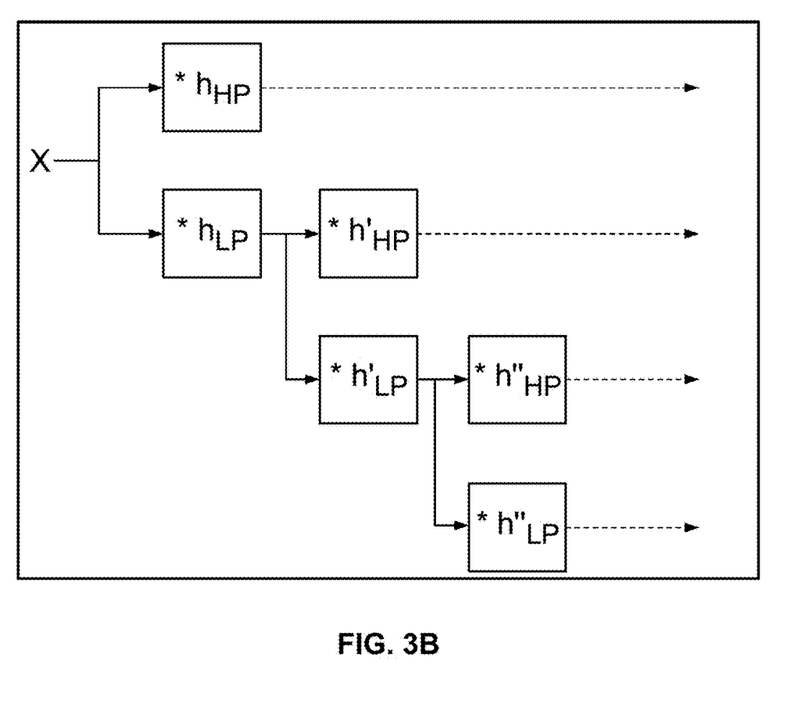

FIGS. 3A and 3B show illustrative diagrams of the exemplary denoising stage. In some embodiments, the result of the denoising is the wavelet transform coefficients called approximations and details. Specifically, the deconstructed filtered PCG output can be reconstructed using the details: $D_j(n)$, $j=1, \ldots, N$ and the approximation $A_j(n)$ to form the denoised filtered PCG output.

In some embodiments, the denoised filtered PCG output is determined based on equation 1:

$$y_r(n) = A_N(n) + \Sigma_{j=1}^{N} D_j(n) \qquad (1).$$

Specifically, initially, in the first step of the denoising, all details that most likely do not carry information of the heartbeat signal are set to 0, for example but not limited to: $D\_j(n)=0$, $j=1, 2, 3, 5, 6, \ldots, N$. For example, details that do not contain sound data corresponding to S1 and/or S2 phases of the cardiac contraction cycle.

Then, the remaining detail, the fourth detail, is thresholded using a threshold calculated utilizing, for example but not limited to, Stein's Unbiased Risk Estimate (SURE) method illustrated by equation 2:

$$D_4(n) = \begin{cases} 0 \forall & D_4(n) < TH_{SURE} \\ D_4(n) & \text{Otherwise} \end{cases} \qquad (2)$$

In some embodiments, the threshold can be calculated using any other similarly suitable method.

In some embodiments the remaining detail can be any of the details or a combination of them.

Lastly, the denoised filtered PCG output is calculated using equation (1).

Stage 3: ICA Transformation

Referring to FIG. 2, (1) the filtered PCG output and (2) the denoised filtered PCG output are further transformed using at least one ICA algorithm to form (1) the transformed filtered PCG output and (2) the transformed denoised filtered PCG output, respectively. In some embodiments, the exemplary ICA algorithm is, for example but not limited to, the FAST ICA algorithm. In some embodiments, the FAST ICA algorithm is, for example, utilized in accordance with "*Independent component analysis: Algorithms and applications*," Hyvärinen et al., *Neural Networks* 13 (4-5): 411-430 (2000), whose specific descriptions are hereby incorporated herein for such specific purpose.

The term "transformation(s)" as used herein refers to linear or non-linear mathematical transformations, which may include, inter alia, digital filtering, mathematical linear or non-linear decomposition, mathematical optimization.

Stage 4: Detection of Fetal and Maternal Heart Beats

To summarize, at this stage, all outputs of the filterbank, denoisng, and ICA, from the previous three stages are being utilized as a S number of detection heartbeat (DH) inputs, where S is a number of all outputs of the filterbank, denoisng, and ICA stages, calculated as L×M, as determined below:

1) M filtered PCG outputs, resulted from 4 signal data inputs of the acoustic sensors M1-M4 being passed through L bandpass filters;
2) M filtered ICA transforms of the filtered PCG outputs;
3) M denoised filtered PCG outputs; and
4) M denoised filtered ICA transforms of the denoised filtered PCG outputs, where M=L×K.

In some embodiments, the exemplary inventive system of the present detection assumes that the heart beats of the mother and/or the fetus(es) can be detected in each one of these DH inputs. In some embodiments, the exemplary inventive system has no prior historical data to suggest in which of these DH inputs the heartbeat of the fetus(es) would be detected, or the heartbeat of the mother, or both, or none.

For example, in some embodiments, the L number of filters in the filter bank is 6 and the total number of inputs for stage 4 is M×L=96.

In some embodiments, the stage 4 is further divided into four sub-stages:

Sub-stage 1: Detect all heartbeats in each of the DH inputs;

Sub-stage 2: Calculate a confidences score that describes the probability that the heartbeats detected in Step 1 are actual heartbeats and not the noise;

Sub-stage 3: Divide all the DH inputs into at least two groups:
  Group 1: fetal heartbeat outputs that contain fetal heartbeats
  Group 2: maternal heartbeat outputs that contain maternal heartbeats;

Sub-stage 4: Select from each group the most probable output that contains the corresponding heartbeat.

Sub-Stage 1: Heartbeat Detection

Typically, acoustic signal can contain at least some noise and heartbeats in at least some cases can be "covered" with noise or in a very noisy surrounding. In addition, typically, the heartbeat morphology can vary form one heartbeat to the next. In some embodiments, the Sub-stage 1 is carried out in at least the following number of steps.

Figure 4:
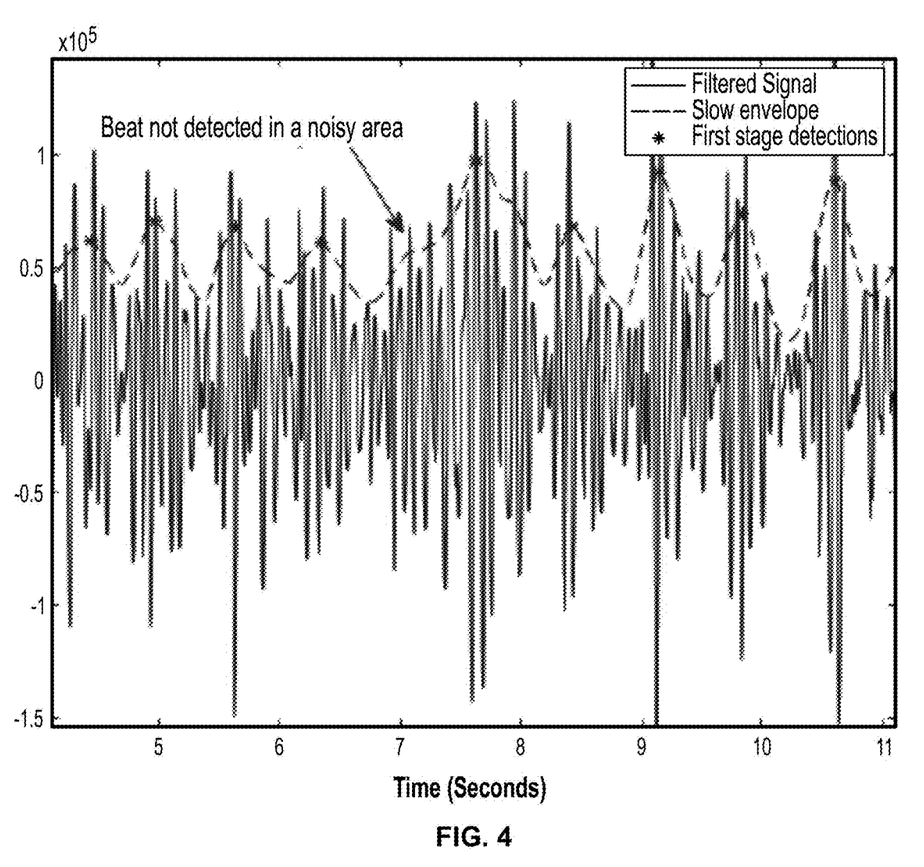
FIGS. 4-8 show graphs illustrating results of processing of data from acoustic sensors according to some embodiments of the present invention.

Step 1: Beat Detection i) In some embodiments, the exemplary inventive system of the present invention calculates a slow envelope of the absolute of the Hilbert transform of the acoustic signal. For instance, exemplary inventive system of the present invention calculates this envelope by applying a moving average filter on the absolute value of the Hilbert transform. In some embodiments, the exemplary inventive system of the present invention can utilize the moving average window having a predetermined length of P. For example, in some embodiments, P is 300 milliseconds (ms). In some embodiments, P varies from 100 to 500 ms. In some embodiments, P varies from 200 to 500 ms. In some embodiments, P varies from 300 to 500 ms. In some embodiments, P varies from 400 to 500 ms.

ii) The exemplary inventive system of the present invention then determines all the peaks of the signal by identifying the zero crossings of the derivative of the signal in each respective DH input.

iii) The exemplary inventive system of the present invention then discards all peaks that are not prominent enough, based, at least in part, on the following criteria used is:

$$\text{Select } \forall \text{ peaks such that } \frac{p(k)}{\text{median}([p(1), p(2), \ldots, p(N)])} > \text{Thresh } k = 1 \ldots N \text{ where } p(k) \text{ is the prominence of the } k^{th} \text{ peak.}$$

iv) The exemplary inventive system of the present invention then groups all peaks into two groups according to, for example, shape and size. For example, such grouping is done using a Gaussian Mixture model clustering algorithm with the following features for each peak:
  the width of each peak divided by the max peak width, and
  the height of the peak divided by its prominence.

v) The exemplary inventive system of the present invention then selects a group of peaks that has the smallest variance measure as the peaks for the next steps.

vi) The exemplary inventive system of the present invention then repeats steps i-v using an average window length R ms. In some embodiments, the average window length of 250 ms. In some embodiments, the average window length is between 100-300 ms.

vii) The exemplary inventive system of the present invention then calculates the Excess Kurtosis measure of the distribution (an adjusted version of Pearson's kurtosis) for the locations of peaks, and selects the peak locations that provide the smallest Excess Kurtosis. FIG. 4 shows the result of the detection at this step, specifically the beat located in a noisy area is not detected.

viii) From the selected peaks locations, the exemplary inventive system of the present invention then calculates an initial estimate of the average Heart Rate (HR).

Step 2—Enhanced Detection

Figure 5:
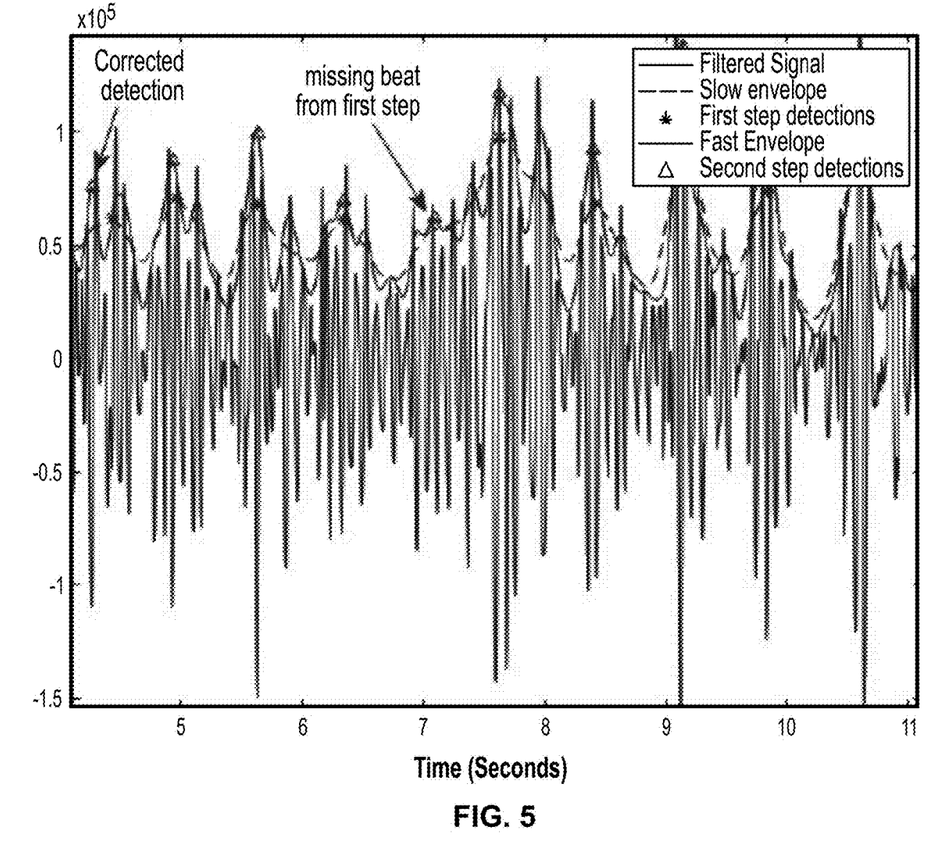

The exemplary inventive system of the present invention refines the detection results of Step 1 by, for example, adding missing beats and correcting the Step 1 detection locations.

i) The exemplary inventive system of the present invention calculates a fast envelope using a Q ms window in the same manner performed as detailed in item (i) of Step 1. For example, in some embodiments, Q is 100 ms. In some embodiments, Q varies between 50-200 ms. In some embodiments, Q varies between 50-150 ms. In some embodiments, Q varies between 50-100 ms.

ii) The exemplary inventive system of the present invention then identifies peaks on the fast envelope signal and selects all prominent peaks in same manner as detailed in item (iii) of Step 1.

iii) The exemplary inventive system of the present invention then calculates all beat to beat intervals (B2B) from the detection results of Step 1, where B2B is an interval between successive beats.

iv) Referring to FIG. 5, the exemplary inventive system of the present invention then completes missing beats which are not identified in Step 1, by reiteratively analyzing all beat to beat intervals determined in the item (iii) of Step 2 based on at least the following exemplary, but not limiting, conditions:

if B2B(k) is higher than 1.5×B2B(average) calculated in item (viii) of Step 1, find a peak from the fast envelope which is as close as possible to the last peak found in item (viii) of Step 1+B2B(average).

v) The exemplary inventive system of the present invention then corrects the detection of Step 1, using the fast envelope.

In some embodiments, the exemplary inventive system of the present invention performs Step 2 to the extent necessary to minimize the beat to beat variance.

Sub-Stage 2: Calculate a Confidence Score for the Heartbeat Detection

Figure 6:
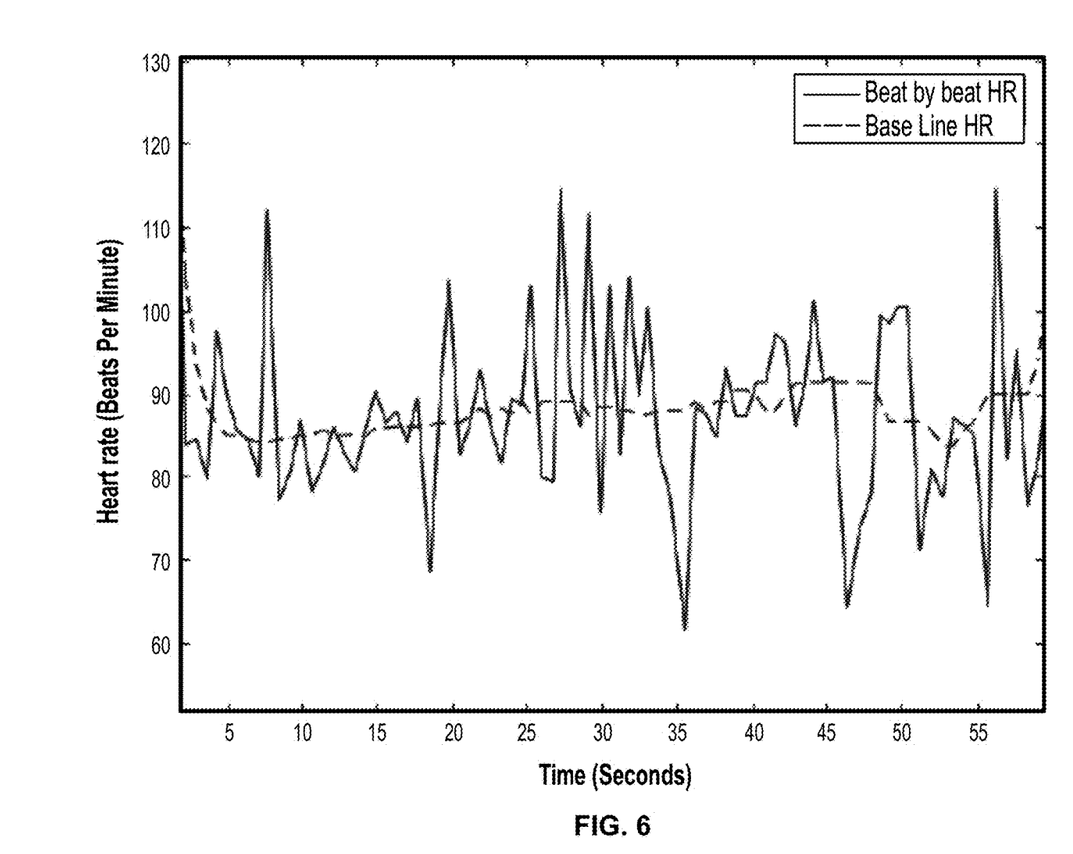

Typically, a beat-by-beat heart rate is a physiological signal which cannot change too fast and usually follows a baseline that defines an average heart rate. In some embodiments, the exemplary inventive system of the present invention utilizes the average heart rate as the base for calculating the confidence score. For each detection of heart beats (for example but not limited to 96 of them, obtained at the end of Sub-Stage 1 from 96 DH inputs), the exemplary inventive system of the present invention calculates the confidence score in accordance with the following steps.

i) The exemplary inventive system of the present invention generates a beat-by-beat heartbeat graph (shown in FIG. 6) based on the locations of the beats.

ii) The exemplary inventive system of the present invention then estimates the heart rate for the whole signal (HRestim), by calculating a histogram of all the beat-by-beat heart rates, where the estimated heart rate for the whole signal is at the maximum of the histogram.

iii) The exemplary inventive system of the present invention then estimates a base line for the beat-by-beat heartbeat graph (FIG. 6) using a median filter (e.g., order 20, etc.).

iv) The exemplary inventive system of the present invention then calculates the confidence score based on the following equation (3):

$$Score = \sqrt{\frac{MfRR^2 + SfRR^2 + OvMP^2}{3}}, \quad (3)$$

where $MfRR = \frac{\sum_{n=1}^{N} |HR(n) - HRestim|}{N}$, $SfRR = std(|HR(n) - HRestim|)$, $OvMP = \frac{1}{N}\sum 1_{HR}$, $1_{HR} = \begin{cases} 1, & |HR(n) - HRestim| < HRestim \times 0.15 \\ 0, & \text{otherwise} \end{cases}$.

Sub-Stage 3: Group all Heartbeat Detections into 2 Groups: Maternal and Fetal

Based on the Stages 1-3 and Sub-stages 1-2, The exemplary inventive system of the present invention generates S beat-by-beat heartbeat graphs, which are vectors representative of the DH inputs obtained from Stages 1-3 (DH input vectors). For example, in case of 96 DH inputs, 96 beat-by-beat heartbeat graphs is generated. Some of the DH input vectors represent maternal heartbeat and some represent the fetal heartbeat.

In some embodiments, the exemplary inventive system of the present invention can utilize, for example, other contemporaneous maternal heartbeat data about the maternal heartbeat which has been separately determined based on data collected from non-acoustic sensor(s)/equipment (e.g., ECG data) to group all DH input vectors that are highly correlated with the other contemporaneous maternal heartbeat data as candidates for maternal heart rate detection and the remaining DH input vectors are grouped as fetal heartbeat candidates.

In some embodiments, when the other contemporaneous maternal heartbeat data is not available, the exemplary inventive system of the present invention can group the DH input vectors, by clustering the estimated heart rate of each DH input vector according to its value. In some embodiments, the exemplary inventive system of the present invention then designates the DH input vectors with a higher average heartbeat rate into the fetal heartbeat group.

Sub-Stage 4: Select the Fetal and Maternal Best Detections

In some embodiments, based on the best confidence score, the exemplary inventive system of the present invention selects the best representative maternal DH input vector as the best detection of the maternal heartbeat rate from the group of the maternal heartbeat DH input vectors identified in Sub-stage 3.

In some embodiments, based on the best confidence score, the exemplary inventive system of the present invention selects the best representative fetal DH input vector as the best detection of the fetal heartbeat rate from the group of the fetal DH input vectors identified in Sub-stage 3.

Figure 7:
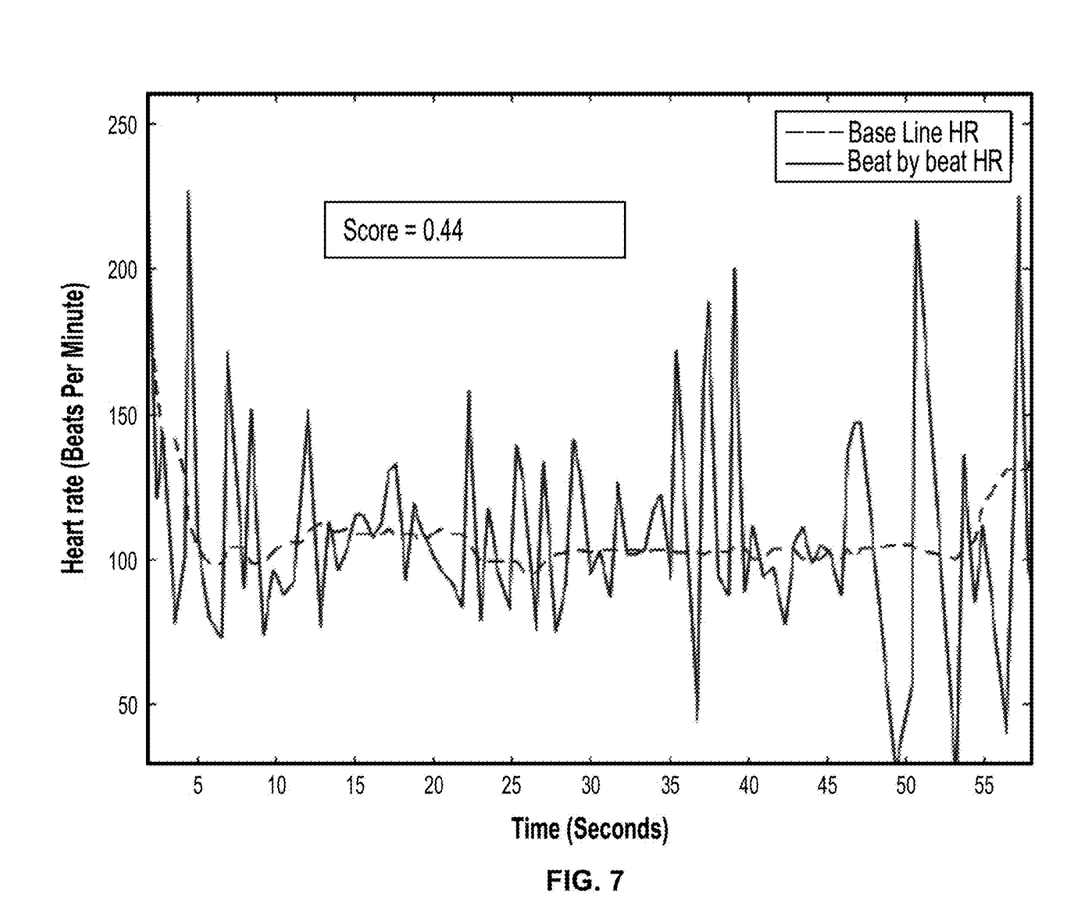

FIG. 7 shows an illustrative example a beat-by-beat heartbeat graph representative of an exemplary DH input vector with a low confidence score.

Figure 8:
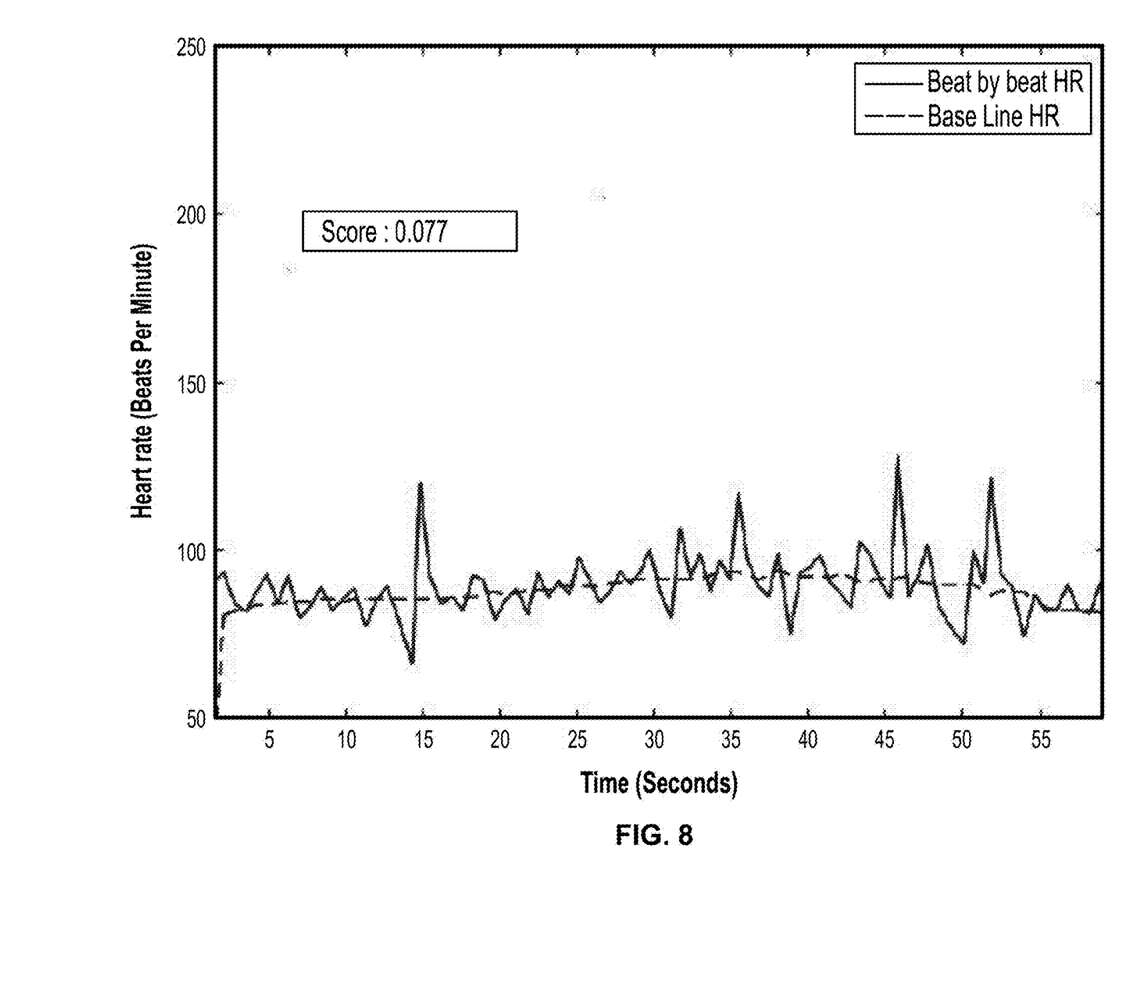

FIG. 8 shows an illustrative example a beat-by-beat heartbeat graph representative of an exemplary DH input vector with a high confidence score.

In some embodiments, the instant invention is directed to a computer-implemented method which includes at least the steps of: receiving, by at least one computer processor executing specific programmable instructions configured for the method, a plurality of Phonocardiogram (PCG) signals data inputs from a plurality of acoustic sensors; digital signal filtering, by the at least one computer processor, utilizing a plurality of bandpass filters, the plurality of PCG signals data inputs to form a plurality of filtered PCG outputs, where the plurality of bandpass filters includes a L number of bandpass filters, where each bandpass filter outputs a K number of filtered PCG outputs; wavelet denoising, by the at least one computer processor, a first subset of filtered PCG outputs of the plurality of filtered PCG outputs to form a M number of denoised filtered PCG outputs, where M is equal to L multiply by K; transforming, by the at least one computer processor, utilizing an Independent-Component-Analysis (ICA), a second subset of filtered PCG outputs of the plurality of filtered PCG outputs to form the M number of filtered ICA transforms; transforming, by the at least one computer processor, utilizing the Independent-Component-Analysis (ICA), a first portion of the second subset of denoised filtered PCG outputs to form the M number of filtered denoised filtered ICA transforms; compiling, by the at least one computer processor, a S number of a plurality of detection heartbeat (DH) inputs, including: i) the M number of filtered PCG outputs, ii) the M number of denoised filtered PCG outputs, iii) the M number of filtered ICA transforms, and iv) the M number of denoised filtered ICA transforms; detecting, by the at least one computer processor, beat locations of beats in each of DH inputs; calculating, by the at least one computer processor, a confidence score that describes a probability that the beats in each DH input of the plurality of DH inputs represent actual heartbeats and not a noise; dividing, by the at least one computer processor, the plurality of DH inputs into at least two groups: i) a first group of DH inputs containing fetal heartbeats, ii) a second group of DH inputs containing maternal heartbeats selecting, by the at least one computer processor, from the first group of DH inputs, at least one particular fetal DH input that contains the fetal heartbeat based on a first confidence score of the at least one particular fetal DH input; and selecting, by the at least one computer processor, from the second group of DH inputs, at least one particular maternal DH input that contains the maternal heartbeat, based on a second confidence score of the at least one particular maternal DH input.

In some embodiments, where the wavelet denoising includes at least: deconstructing, by the at least one computer processor, each filtered PCG output to generate a plurality of transform coefficients, by irrelatively passing each filtered PCG output through a succession of low and high pass filters; identifying, by the at least one computer processor, a subset of heartbeat-carrying transform coefficients from the plurality of transform coefficients, reconstructing, by the at least one computer processor, the subset of heartbeat-carrying transform coefficients to form the M number of denoised filtered PCG outputs.

In some embodiments, K is equal to a number of the plurality of acoustic sensors, and L is equal to 6.

In some embodiments, each filter of the plurality of bandpass filters has a bandwidth of 10-100 Hz and a frequency range of 5-110 HZ.

In some embodiments, the detecting of the beat locations of the beats in each of DH inputs includes at least: calculating, by the at least one computer processor, a predetermined transform filter; iteratively repeating, by the at least one computer processor, based on a predetermined average window length of the predetermined transform filter: identifying, in each DH input, a subset of peaks having a predetermined shape and a predetermined size, and selecting a group of peaks from the subset of peaks, where the group of peaks has the smallest variance measure; calculating, by the at least one computer processor, initial locations of the beats.

In some embodiments, the calculating the confidence score includes at least: generating, by the at least one computer processor, a beat-by-beat heartbeat graph for each DH input based on the beat locations.

In some embodiments, the dividing the plurality of DH inputs into the first group of DH inputs containing fetal heartbeats and the second group of DH inputs containing maternal heartbeats includes at least: clustering, by the at least one computer processor, the beats of each DH input according to each beat value; and assigning, by the at least one computer processor, a particular DH input having a higher average beat rate into the first group of DH inputs containing fetal heartbeats.

In some embodiments, the present invention is directed to a specifically programmed computer system, including at least the following components: at least one specialized computer machine, including: a non-transient memory, electronically storing particular computer executable program code; and at least one computer processor which, when executing the particular program code, becomes a specifically programmed computing processor that is configured to at least perform the following operations: receiving a plurality of Phonocardiogram (PCG) signals data inputs from a plurality of acoustic sensors; digital signal filtering, utilizing a plurality of bandpass filters, the plurality of PCG signals data inputs to form a plurality of filtered PCG outputs, where the plurality of bandpass filters includes a L number of bandpass filters, where each bandpass filter outputs a K number of filtered PCG outputs; wavelet denoising a first subset of filtered PCG outputs of the plurality of filtered PCG outputs to form a M number of denoised filtered PCG outputs, where M is equal to L multiply by K; transforming, utilizing an Independent-Component-Analysis (ICA), a second subset of filtered PCG outputs of the plurality of filtered PCG outputs to form the M number of filtered ICA transforms; transforming, utilizing the Independent-Component-Analysis (ICA), a first portion of the second subset of denoised filtered PCG outputs to form the M number of denoised filtered ICA transforms; compiling a S number of a plurality of detection heartbeat (DH) inputs, including: i) the M number of filtered PCG outputs, ii) the M number of denoised filtered PCG outputs, iii) the M number of filtered ICA transforms, and iv) the M number of denoised filtered ICA transforms; detecting beat locations of beats in each of DH inputs; calculating a confidence score that describes a probability that the beats in each DH input of the plurality of DH inputs represent actual heartbeats and not a noise; dividing the plurality of DH inputs into at least two groups: i) a first group of DH inputs containing fetal heartbeats, ii) a second group of DH inputs containing maternal heartbeats; selecting, from the first group of DH inputs, at least one particular fetal DH input that contains the fetal heartbeat based on a first confidence score of the at least one particular fetal DH input; and selecting, from the second group of DH inputs, at least one particular maternal DH input that contains the maternal heartbeat, based on a second confidence score of the at least one particular maternal DH input.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A computer-implemented method, comprising:
receiving, by at least one computer processor executing specific programmable instructions configured for the method, a plurality of Phonocardiogram (PCG) signals data inputs from a plurality of acoustic sensors;
transforming, by the at least one computer processor, utilizing an Independent-Component-Analysis (ICA), at least one first subset of the PCG signals data inputs to form a plurality of ICA transforms;
wavelet denoising, by the at least one computer processor, at least one second subset of the PCG signals data inputs to form a plurality of denoised PCG outputs;
transforming, by the at least one computer processor, utilizing the ICA, the plurality of denoised PCG outputs to form a plurality of denoised ICA transforms;
compiling, by the at least one computer processor, a plurality of detection heartbeat (DH) inputs, wherein the plurality of DH inputs comprises:
i) the plurality of ICA transforms, and
ii) the plurality of denoised ICA transforms;
detecting, by the at least one computer processor, locations of potential heartbeats in each of the DH inputs;
calculating, by the at least one computer processor, a plurality of confidence scores, each of the confidence scores corresponding to one of the potential heartbeats, wherein each of the confidence scores describes a probability that the corresponding one of the potential heartbeats represents an actual heartbeat and not a noise;
selecting, by the at least one computer processor, the ones of the DH inputs that include at least one actual heartbeat;
dividing, by the at least one computer processor, the selected DH inputs into at least two groups:
i) a first group of selected DH inputs containing potential fetal heartbeats, and
ii) a second group of selected DH inputs containing potential maternal heartbeats;
selecting, by the at least one computer processor, from the first group of selected DH inputs, at least one of the plurality of selected DH inputs that contains at least one actual fetal heartbeat, based on the at least one of the plurality of confidence scores corresponding to the at least one of the actual heartbeats included in the at least one of the plurality of selected DH inputs;
selecting, by the at least one computer processor, from the second group of selected DH inputs, at least one of the plurality of selected DH inputs that contains at least one actual maternal heartbeat, based on the at least one of the plurality of confidence scores corresponding to the at least one of the actual heartbeats included in the at least one of the plurality of selected DH inputs; and
outputting at least one visual indication corresponding to at least one of (a) the at least one actual maternal heartbeat and (b) the at least one actual fetal heartbeat.

2. The computer-implemented method of claim 1, wherein the wavelet denoising comprises:
deconstructing, by the at least one computer processor, each PCG signals data input to generate a plurality of transform coefficients, by iteratively passing each PCG signals data input through a succession of low and high pass filters;
identifying, by the at least one computer processor, a subset of heartbeat-carrying transform coefficients from the plurality of transform coefficients,
reconstructing, by the at least one computer processor, the subset of heartbeat-carrying transform coefficients to form the plurality of denoised PCG outputs.

3. The computer-implemented method of claim 1, wherein the detecting of the beat locations of the beats in each of the DH inputs comprises:
calculating, by the at least one computer processor, a predetermined transform filter;
iteratively repeating, by the at least one computer processor, based on a predetermined average window length of the predetermined transform filter, the steps of:
identifying, in each DH input, a subset of peaks having a predetermined shape and a predetermined size, and
selecting a group of peaks from the subset of peaks, wherein the group of peaks has the smallest variance measure;
calculating, by the at least one computer processor, initial locations of the beats.

4. The computer-implemented method of claim 1, wherein the calculating the confidence score comprises:
generating, by the at least one computer processor, a beat-by-beat heartbeat graph for each DH input based on the locations of the potential heartbeats.

5. The computer-implemented method of claim 1, wherein the dividing the plurality of selected DH inputs into the first group of selected DH inputs containing potential fetal heartbeats and the second group of selected DH inputs containing selected maternal heartbeats comprises:
clustering, by the at least one computer processor, the beats of each DH input according to each beat value; and
assigning, by the at least one computer processor, the selected DH inputs having a higher average beat rate into the first group of selected DH inputs containing fetal heartbeats.

6. A specifically programmed computer system, comprising:
at least one specialized computer machine, comprising:
a non-transient memory, electronically storing computer executable program code; and
at least one computer processor which, when executing the program code, becomes a specifically programmed computing processor that is configured to at least perform the following operations:
receiving a plurality of Phonocardiogram (PCG) signals data inputs from a plurality of acoustic sensors;
transforming, utilizing an Independent-Component-Analysis (ICA), at least one first subset of the PCG signals data inputs to form a plurality of ICA transforms;
wavelet denoising at least one second subset of the PCG signals data inputs to form a plurality of denoised PCG outputs;
transforming, utilizing the ICA, the plurality of denoised PCG outputs to form a plurality of denoised ICA transforms;
compiling a plurality of detection heartbeat (DH) inputs, wherein the plurality of DH inputs comprises:
i) the plurality of ICA transforms, and
ii) the plurality of denoised ICA transforms;
detecting locations of potential heartbeats in each of the DH inputs;
calculating a plurality of confidence scores, each of the confidence scores corresponding to one of the potential heartbeats, wherein each of the confidence scores describes a probability that the corresponding one of the potential heartbeats represents an actual heartbeat and not a noise;
selecting the ones of the DH inputs that include at least one actual heartbeat;
dividing the selected of DH inputs into at least two groups:
i) a first group of selected DH inputs containing potential fetal heartbeats, and
ii) a second group of selected DH inputs containing potential maternal heartbeats;
selecting, from the first group of selected DH inputs, at least one of the plurality of selected DH inputs that contains at least one actual fetal heartbeat, based on the at least one of the plurality of confidence scores corresponding to the at least one of the actual heartbeats included in the at least one of the plurality of selected DH inputs;
selecting, from the second group of selected DH inputs, at least one of the plurality of selected DH inputs that contains at least one actual maternal heartbeat, based on the at least one of the plurality of confidence scores corresponding to the at least one of the actual heartbeats included in the at least one particular maternal DH input of the plurality of selected DH inputs; and
outputting at least one visual indication corresponding to at least one of (a) the at least one actual maternal heartbeat and (b) the at least one actual fetal heartbeat.

7. The specifically programmed computer system of claim 6, wherein the wavelet denoising comprises:
   deconstructing each PCG signals data input to generate a plurality of transform coefficients, by iteratively passing each PCG signals data input through a succession of low and high pass filters;
   identifying a subset of heartbeat-carrying transform coefficients from the plurality of transform coefficients,
   reconstructing the subset of heartbeat-carrying transform coefficients to form the plurality of denoised PCG outputs.

8. The specifically programmed computer system of claim 6, wherein the detecting of the beat locations of the beats in each of the DH inputs comprises:
   calculating a predetermined transform filter;
   iteratively repeating, based on a predetermined average window length of the predetermined transform filter, the steps of:
      identifying, in each DH input, a subset of peaks having a predetermined shape and a predetermined size, and
      selecting a group of peaks from the subset of peaks, wherein the group of peaks has the smallest variance measure;
   calculating initial locations of the beats.

9. The specifically programmed computer system of claim 6, wherein the calculating the confidence score comprises:
   generating a beat-by-beat heartbeat graph for each DH input based on the locations of the potential heartbeats.

10. The specifically programmed computer system of claim 6, wherein the dividing the plurality of selected DH inputs into the first group of selected DH inputs containing fetal heartbeats and the second group of selected DH inputs containing maternal heartbeats comprises:
   clustering the beats of each DH input according to each beat value; and
   assigning the selected DH inputs having a higher average beat rate into the first group of selected DH inputs containing fetal heartbeats.

* * * * *